(12) United States Patent
Rohling

(10) Patent No.: US 8,696,582 B2
(45) Date of Patent: Apr. 15, 2014

(54) APPARATUS AND METHOD FOR IMAGING A MEDICAL INSTRUMENT

(75) Inventor: Robert Rohling, Vancouver (CA)

(73) Assignee: The University of British Columbia, Vancouver, British Columbia (CA)

( * ) Notice: Subject to any disclaimer, the term of this patent is extended or adjusted under 35 U.S.C. 154(b) by 24 days.

(21) Appl. No.: 13/206,972

(22) Filed: Aug. 10, 2011

(65) Prior Publication Data

US 2012/0289820 A1 Nov. 15, 2012

Related U.S. Application Data

(60) Provisional application No. 61/484,373, filed on May 10, 2011.

(51) Int. Cl.
*A61B 8/14* (2006.01)

(52) U.S. Cl.
USPC .......................................... 600/459; 600/463

(58) Field of Classification Search
USPC ............................ 600/437–469; 382/128–132
See application file for complete search history.

(56) References Cited

U.S. PATENT DOCUMENTS

| | | | |
|---|---|---|---|
| 4,475,553 A | 10/1984 | Yamaguchi et al. | |
| 4,635,644 A | 1/1987 | Yagata | |
| 5,226,113 A | 7/1993 | Cline et al. | |
| 5,787,889 A | 8/1998 | Edwards et al. | |
| 6,048,312 A | 4/2000 | Ishrak et al. | |
| 6,336,899 B1 * | 1/2002 | Yamazaki | 600/443 |
| 6,616,610 B2 * | 9/2003 | Steininger et al. | 600/443 |
| 7,828,733 B2 * | 11/2010 | Zhang et al. | 600/437 |
| 7,916,139 B2 | 3/2011 | Murray et al. | |
| 8,162,833 B2 * | 4/2012 | Zhang et al. | 600/437 |
| 2002/0082518 A1 | 6/2002 | Weiss et al. | |
| 2004/0267121 A1 * | 12/2004 | Sarvazyan et al. | 600/439 |
| 2010/0256483 A1 * | 10/2010 | Wall et al. | 600/424 |

FOREIGN PATENT DOCUMENTS

| | | |
|---|---|---|
| GB | 2400176 | 10/2004 |
| JP | 2000-185041 | 7/2000 |

OTHER PUBLICATIONS

Lacroute, Philippe G., "Fast Volume Rendering Using a Shear-Wrap Factorization of the Viewing Transformation", Department of Electrical Engineering and Computer Science, Stanford University, Sep. 1995.

Grau, Thomas et al., "Paramedian Access to the Epidural Space: The Optimum Window for Ultrasound Imaging"; Journal of Clinical Anesthesia, vol. 13, pp. 123-217, 2001.

Tran, Denis et al., "Preinsertion Paramedian Ultrasound Guidance for Epidural Anesthesia"; International Anesthesia Research Society; vol. 109, No. 2, pp. 661-667, Aug. 2009.

\* cited by examiner

*Primary Examiner* — Sanjay Cattungal
(74) *Attorney, Agent, or Firm* — Troutman Sanders LLP; Ryan A. Schneider

(57) ABSTRACT

The invention provides an ultrasound imaging and medical instrument guiding apparatus, a system for acquiring and displaying ultrasound medical images and methods of using the apparatus and system in epidural anesthetic procedure. The apparatus comprises a hand-held ultrasound probe, configured to acquire a volumetric dataset representing a 3-D depiction of a volume; a mount to which the probe is mounted; and a medical instrument guide positionable relative to the ultrasound probe and configured to receive and guide a medical instrument along a propagation axis to a target in a body such that the target and the propagation axis intersect in the volume. The volumetric dataset acquired by the hand-held ultrasound probe comprises information about the medical instrument's position relative to the target in three dimensions and the medical instrument guide has a visible mark from which the depth of the medical instrument insertion along the propagation axis can be referenced.

34 Claims, 15 Drawing Sheets

APPARATUS AND METHOD FOR IMAGING A MEDICAL INSTRUMENT

CROSS-REFERENCE TO RELATED APPLICATIONS

This application claims the benefit of U.S. Provisional Application No. 61/484,373 filed 10 May 2011, the entire contents and substance of which are hereby incorporated by reference.

BACKGROUND OF THE INVENTION

1. Field of the Invention

This invention relates generally to medical imaging, and particular to an apparatus and method for imaging a medical instrument, particularly while being inserted inside a patient.

2. Description of Related Art

Some medical procedures require a needle or needle-like instrument to be inserted into a patient's body to reach a target. Examples of these procedures include tissue biopsies, drug delivery, drainage of fluids, ablation for cancer treatment, and catheterization. Some of these procedures can be done manually without any additional guidance other than the sense of feel and visualization of the surface of the body. Other procedures are difficult to perform without additional guidance because the target is deep, the target is small, sense of feel is inadequate for recognizing when the needle's tip has reached the target, or there is a lack of visual landmarks on the body surface. In those cases, providing the health care provider with an image of the interior of the body in the vicinity of the target would be beneficial. It would be particularly beneficial to provide real-time images of both the target and the needle as it progresses towards the target.

A particularly challenging needle insertion procedure is required in epidural anesthesia, often referred to as an "epidural" in the field of obstetrics. Epidural anesthesia is administered in the majority (>80% of women in labor) of patients for pain relief of labor and delivery in North American hospitals. Epidural anesthesia involves the insertion of a needle into the epidural space in the spine. The anatomy of the back and spine, in order of increasing depth from the skin, includes the skin and fat layers, a supraspinous and interspinous ligament, the epidural space, the dura mater and spinal cord. A doctor must insert the needle through these layers in order to reach the epidural space without over-inserting the needle and puncturing the thin dura mater surrounding the spinal cord.

The traditional procedure of epidural needle insertion will now be described. The patient is seated with the doctor facing the patient's back. The doctor chooses a puncture site between the vertebrae based on feeling the protruding spinal processes. After choosing an insertion point on the skin, the doctor typically inserts the needle in a plane midline with the long axis of the spine. A saline-filled syringe is attached to the needle so the doctor can apply pressure to the plunger of the syringe, as the needle in incrementally advanced toward the epidural space, and feel how easily saline is injected into the tissue. This is called the "loss-of-resistance" method because resistance falls when the needle tip enters the epidural space. In this way, the sense of feel is the main method for determining when the needle tip has reached the epidural space because the saline is easily injected into the epidural space compared to the tissue encountered before the epidural space. This method can result in failure rates of 6 to 20% depending on the experience and training of the health care provider. Complications include inadvertent dura puncture resulting in loss of cerebral spinal fluid and headache, as well as nerve injury, paralysis and even death. Image guidance during needle insertion would improve the accuracy of needle insertion by providing better feedback to the doctor of where the needle is located with respect to the anatomical structures including the target.

In the past several years, ultrasound has been explored as a means to provide a pre-puncture estimate of the depth of the epidural space to correctly place the needle tip. This entails an ultrasound scan prior to needle insertion so that the doctor uses the knowledge of how deep to expect the epidural space when inserting the needle. This use of ultrasound at the planning stage for epidural guidance has received wide interest from the anesthesia community. It is called pre-puncture scanning because the ultrasound is used before, but not during, needle insertion. The National Institute for Health and Clinical Excellence (NICE) has recently issued full guidance to the NHS in England, Wales, Scotland and Northern Ireland on ultrasound-guided catheterization of the epidural space (January, 2008). While pre-puncture scanning is a useful advance, doctors still face challenges associated with performing needle insertion procedures without information provided by real-time imaging.

There have been some published reports of providing real-time ultrasound imaging for needle insertion procedures. However, none of these approaches have proven to be entirely satisfactory. Problems include overly limiting views of the images of the target and needle due to poor reflection of ultrasound waves, and/or inherent limitations in the ultrasound equipment.

SUMMARY

It is an object of the invention to provide a solution to at least some of the deficiencies in the prior art.

According to one aspect of the invention, there is provided an ultrasound imaging and medical instrument guiding apparatus comprising: a hand-held ultrasound probe, configured to acquire a volumetric dataset representing a 3-D depiction of a volume; a mount to which the probe is mounted; and a medical instrument guide positionable relative to the ultrasound probe and configured to receive and guide a medical instrument along a propagation axis to a target in a body such that the target and the propagation axis intersect in the volume. The volumetric dataset acquired by the hand-held ultrasound probe comprises information about the medical instrument's position relative to the target in three dimensions and the medical instrument guide has a visible mark from which the depth of the medical instrument insertion along the propagation axis can be referenced.

The probe can be a mechanical 3-D probe or a multidimensional probe. The probe can also be curved so that it can produce a diverging set of beams. In this way, a wide field of view of the anatomy can be obtained with a relatively small footprint of the probe. Moreover, the probe can be angled towards the propagation axis, so that the beams intersect the needle at angles closer to perpendicular.

The mount can be a housing that houses the probe and the medical instrument guide is a channel extending through the housing. The medical instrument guide may be detachably mountable to the mount in one or more orientations.

The apparatus may further comprise a grommet that can be attached to the medical instrument at a location relative to the visible mark thereby indicating a desired depth of the medical instrument insertion.

The medical instrument guide may include means for tracking the position of the instrument relative to the probe.

The hand-held ultrasound probe can be configured to acquire the volumetric dataset continuously so that the volumetric dataset comprises real-time or semi-real-time information about the medical instrument's position relative to the target in three dimensions. Moreover, the ultrasound probe may also be configured to acquire the volumetric dataset for the smallest volume that encloses the medical instrument and the target.

The mount may further have a second contact that is to be in contact with the body in addition to the probe. In this way, the second contact point can provide additional stability for the apparatus with respect to the patient.

The mount may also have markings representing the inferior-superior and left-right axes of the body thereby indicating the desired position of the apparatus on the body. In this way, the operator can easily figure out the orientation and position the apparatus onto the body.

According to another aspect of the invention, there is provided a system for acquiring and displaying ultrasound medical images. The system includes an ultrasound imaging and instrument guiding apparatus and circuitry communicative with the ultrasound imaging and instrument guiding apparatus. The ultrasound imaging and instrument guiding apparatus has a hand-held ultrasound probe, configured to acquire a volumetric dataset representing a 3-D depiction of a volume; a mount to which the probe is mounted; and a medical instrument guide positionable relative to the ultrasound probe and configured to receive and guide a medical instrument along a propagation axis to a target in a body such that the target and the propagation axis intersect in the volume. The circuitry is communicative with the ultrasound imaging and instrument guiding apparatus to receive the volumetric dataset therefrom and comprises a processor with a memory having programmed thereon steps and instructions for execution by the processor to: condition the volumetric datasets; calculate an image plane that coincides with the propagation axis; create a thick-slice image, wherein the thick-slice image represents data from a slab of non zero thickness of the volume encompassing the calculated image plane; and a display device communicative with the circuitry to receive and display one or more of the thick-slice images.

The memory can be further programmed to enhance the thick-slice image. Moreover, the memory can be further programmed to superimpose a graphical overlay representing the propagation axis of the instrument on the image.

The medical instrument guide may have a visible mark from which the depth of the medical instrument insertion along the propagation axis can be referenced and the memory can be further programmed to superimpose a graphical overlay representing an anticipated trajectory of the medical instrument including graduations indicating the depth of the medical instrument insertion with respect to the visible mark on the medical instrument guide.

The system may also include a storage device to record the thick-slice image.

The thick slice of the volume may be oriented in the sagittal plane or in the transverse plane of the body, or multiple images may be created to cover thick slices in both sagittal and transverse planes.

The thick slice image can be created from the thick slice of the volume by a process of merging data in a direction perpendicular to the cross-sectional plane of the thick slice.

The size of the volume acquired by the probe can be determined in a manner that it minimally encompasses the maximum extents of the thick slice used to create the image. In this way, the probe can acquire the smaller volume faster and the smaller volume can be processed by the circuit faster.

The visible mark of the medical instrument guide may be referenced to show the depth of the thick slice of the volume along the propagation axis. In this way, the visible mark readings on the medical instrument guide and the displayed depth can work in collaboration.

According to another aspect of the invention, there is provided a method of using the above apparatus in an epidural anesthetic procedure. The method comprises: placing the apparatus over a back of a patient such that the medical instrument guide is placed over a needle insertion point on the back, and emitting an ultrasound signal into the back and capturing an image of the volume, wherein the image of the volume includes a section of the patient's spine.

The target can be an epidural space. The probe can be placed at a paramedian location with respect to the spine. Moreover, the probe can be placed over spinae erector muscles of the patient. In this way, the muscle tissue may serve as a "window" that transmits ultrasound particularly well.

The image plane can be approximately in the mid-sagittal plane of the spine or is approximately perpendicular to the long axis of the spine. Multiple image planes may also be obtained to be approximately in the mid-sagittal plane of the spine and approximately perpendicular to the long axis of the spine respectively.

The method may further comprise inserting a needle through the medical instrument guide and along the propagation axis that intersects the target, such that the captured images include an image of the needle. Moreover, the method may further comprise performing a loss-of-resistance procedure to confirm entry of the needle tip into the epidural space. The method may also comprise removing the needle from the medical instrument guide and performing a loss-of-resistance procedure to confirm entry of the needle tip into the epidural space.

The method may further comprise placing the apparatus paramedian to the sacrum and sliding the apparatus in the cranial-caudal direction while counting the vertebrae displayed on the image and stopping at the location where the medical instrument guide is placed over the needle insertion point on the back. Alternatively, the method may also comprise placing the apparatus paramedian to the twelfth vertebrae and sliding the apparatus in the cranial-caudal direction while counting the vertebrae displayed on the image and stopping at the location where the medical instrument guide is placed over the needle insertion point on the back.

The probe may also be placed along the midline centre of the spine and the image of the volume is created from a thick slice of the volume approximately perpendicular to the long axis of the spine.

The medical instrument guide may have a visible mark from which the depth of the medical instrument insertion along the propagation axis can be referenced and the memory may be further programmed to superimpose a graphical overlay representing an anticipated trajectory of the medical instrument including graduations indicating the depth of the medical instrument insertion with respect to the visible mark on the medical instrument guide. The method may further comprise: observing the depth of the target according to the graduations on the graphic overlay with respect to the visible mark on the medical instrument guide; inserting the medical instrument through the medical instrument guide, wherein the medical instrument has a plurality of equally spaced etchings; and stopping the medical instrument insertion when the depth of the medical instrument insertion, as indicated by the number of the etchings that passed the visible mark, equals the depth of the target. Alternatively the method may also comprise: observing the depth of the target according to the graduations on the graphic overlay with respect to the visible mark on the medical instrument guide; attaching the grommet to the medical instrument at a distance from the inserted tip of the instrument that is equal to the depth of the target with respect to the visible mark on the medical instrument guide; inserting the medical instrument through the medical instrument guide; and stopping the medical instrument insertion when the depth of the medical instrument insertion, as indicated by the distance from the grommet to the visible mark on the medical instrument guide, equals the depth of the target.

According to another aspect of the invention, there is provided a method of using the above referenced system, i.e. the system which includes an ultrasound imaging and instrument guiding apparatus and circuitry communicative with the ultrasound imaging and instrument guiding apparatus. This method comprises: placing the apparatus over a back of a patient such that the medical instrument guide is placed over a needle insertion point on the back, and emitting an ultrasound signal into the back and acquiring a volumetric dataset representing a 3-D depiction of a volume, wherein the dataset includes a section of the patient's spine. The method further comprises conditioning the volumetric datasets, calculating an image plan that coincides with the propagation axis, and creating a thick-slice image, wherein the thick-slice image represents data from a slab of non zero thickness of the volume encompassing the calculated image plane, and displaying one or more of the thick-slice images.

This method can further comprise superimposing a graphical overlay representing the propagation axis of the instrument on the image. The method can also further comprise recording the thick slice image onto a storage device. Further, the method can comprise creating the image from the thick slice of the volume by a process of merging data in a direction perpendicular to the cross-sectional plane of the thick slice.

DETAILED DESCRIPTION

Other aspects and features of the present invention will become apparent to those ordinarily skilled in the art upon review of the following description of illustrative embodiments in conjunction with the accompanying figures.

Ultrasound imaging is a technique for imaging the interior of the body with high frequency sound waves. A standard ultrasound probe comprises a set of transducer elements emitting sound waves into the body. The sound waves reflect on tissue or bone in the body and the reflected sound (echo) is detected by the same transducer elements. By calculating the time from emission to detection of the sound waves at each transducer and measuring the intensity of the reflected sound wave, an ultrasound image can be constructed that shows various anatomical features in the ultrasound probe's field of view.

Ultrasound scanning during a needle insertion procedure enables the observation of both the needle and the target on a real-time ultrasound display. One advantage of such an ultrasound scanning-assisted needle insertion procedure is the ability for the doctor to modify the path of needle insertion to correct the trajectory towards the target. Embodiments of the invention described herein relate to an ultrasound imaging and needle guiding apparatus for guiding a needle to a target in a patient's body, such as the epidural space of the spine, and for acquiring real-time ultrasound images of the needle and target. Specifically, these described embodiments provide real-time or near real-time images of both the needle and the surrounding tissue and bone of the body using a 3-D ultrasound probe while the needle is being inserted through a medical instrument guide. In some embodiments, there is an ultrasound imaging and needle guiding apparatus with a 3-D ultrasound probe which is placed in a slightly paramedian position, relative to a midline needle insertion position, which enables the ultrasound imaging and needle guiding apparatus to clearly view both the needle and the target, such as an epidural space. In addition, some of the described embodiments include a method for using the ultrasound imaging and needle guiding apparatus and for processing acquired 3-D volumetric datasets from the ultrasound probe for representation on a 2-D display.

Directional terms such as "top", "bottom", "left" and "right" are used in the following description for the purposes of providing relative reference only, and are not intended to suggest any limitations on how any apparatus or components thereof are to be manufactured or positioned during use. A number of preferred embodiments will now be described by way of example only.

Figure 4:
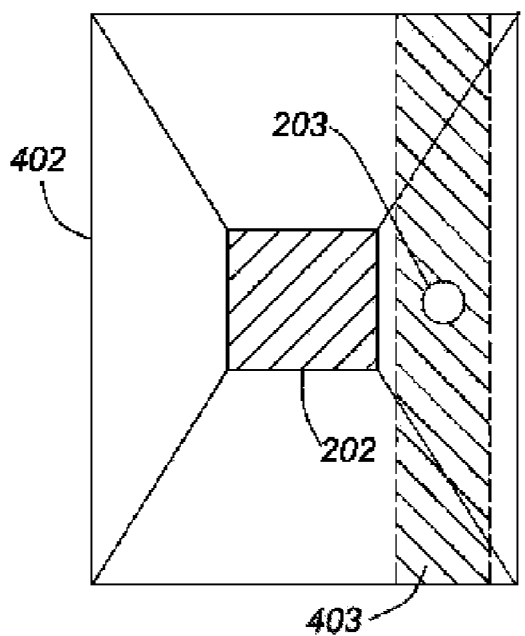
FIG. 4(a) is a schematic back view of the ultrasound probe of the ultrasound imaging and needle guiding apparatus along with a representation of the thick slice in the sagittal plane of the ultrasound image captured by the ultrasound probe.
FIG. 4(b) is a schematic back view of the ultrasound probe of the ultrasound imaging and needle guiding apparatus along with a representation of the thick slice in the transverse plane of the ultrasound image captured by the ultrasound probe.
Figure 4:
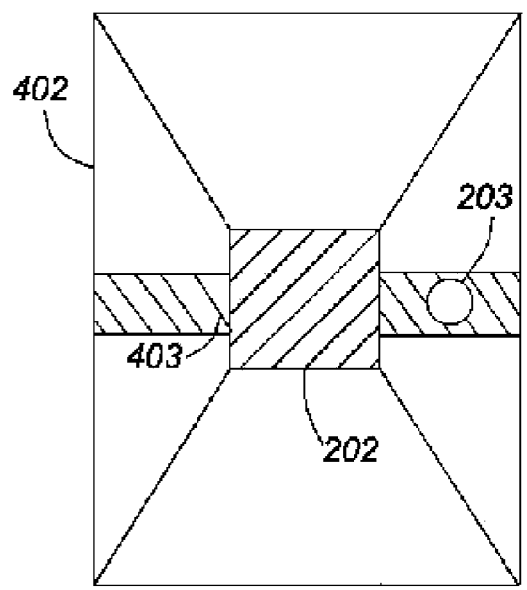
Figure 5:
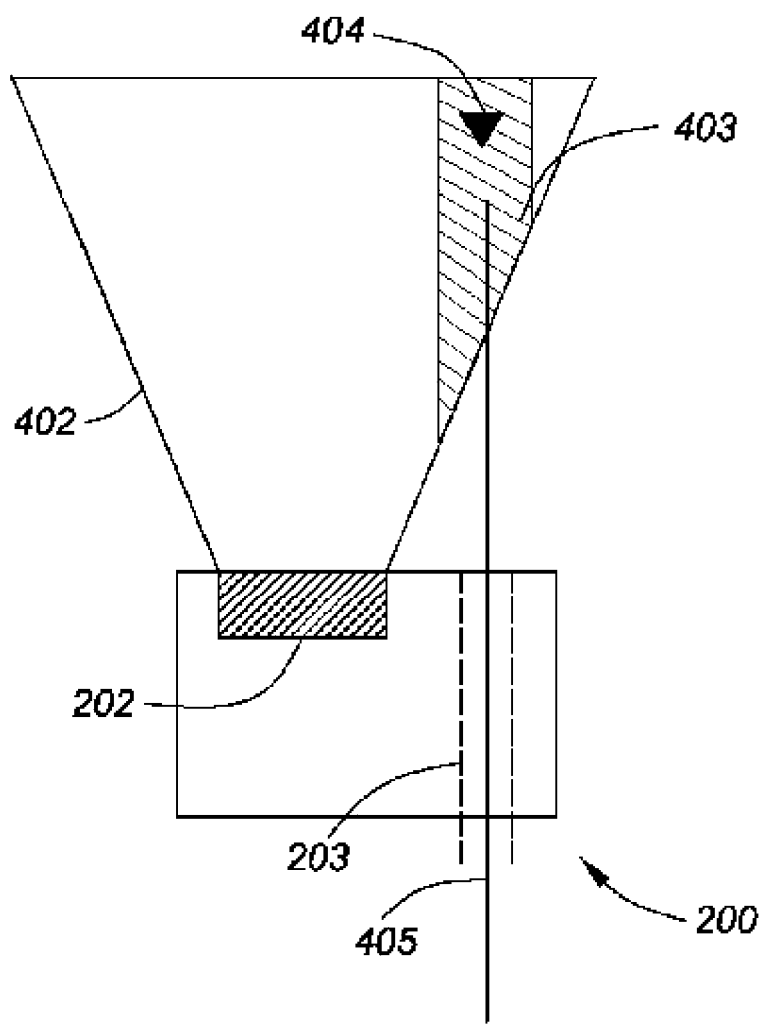
FIG. 5 is a schematic top view of the ultrasound probe of the ultrasound imaging and needle guiding apparatus along with a representation of the spatial extent of the volumetric dataset captured by the ultrasound probe.

According to a first embodiment and referring to FIGS. 2 to 8, there is provided an ultrasound imaging and needle guiding apparatus 200 that enables the acquisition of simultaneous, or near simultaneous, images of anatomical features of a body 101 and a needle 405 (as shown in FIG. 5), ablation probe, catheter, guide wires or other medical instrument that is inserted into the body 101 and guided by the apparatus 200 and towards a target 404. The main components of the apparatus 200 include a 3-D ultrasound probe 202, a mount 199 on the probe 202, and a medical instrument guide 203 that in this embodiment is permanently affixed to the mount 199 but in other embodiments can be detachably mounted to the mount 199 or remotely located. The ultrasound probe 202 is positioned on the mount 199 to provide simultaneous or near-simultaneous 3-D depictions of a volume of interest in the body 101 and of the medical instrument 405 inserted into the volume of interest. The mount 199 in this embodiment is a housing in which probe 202 is housed; alternatively, the mount 199 can be a rectangular mounting plate (not shown) to which the probe 202 is mounted, or a rod or similar-shaped member to which the probe 202 is mounted (not shown).

Figure 9:
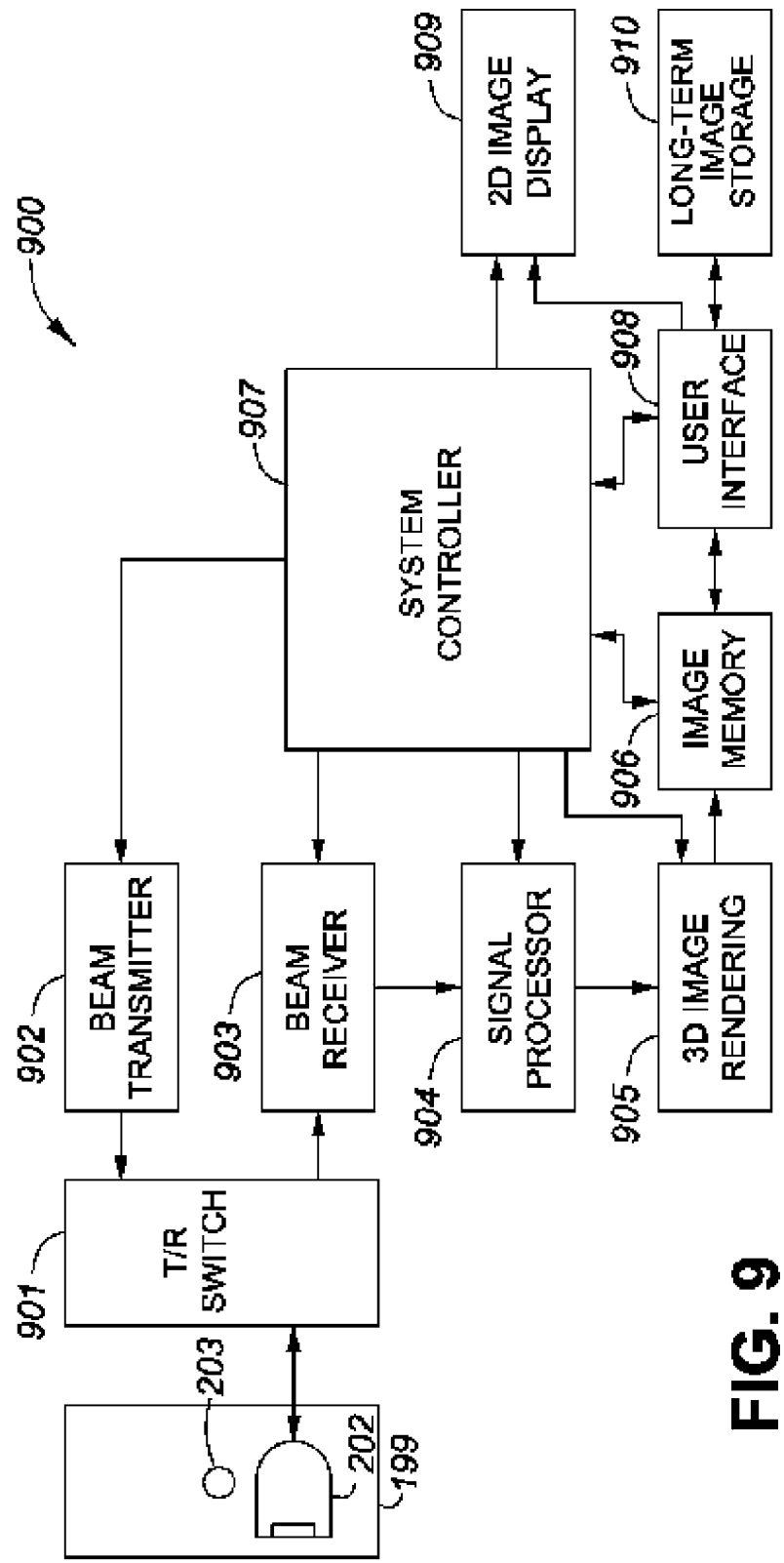
FIG. 9 is a block diagram of an imaging system comprising the ultrasound imaging and needle guiding apparatus.
Figure 11:
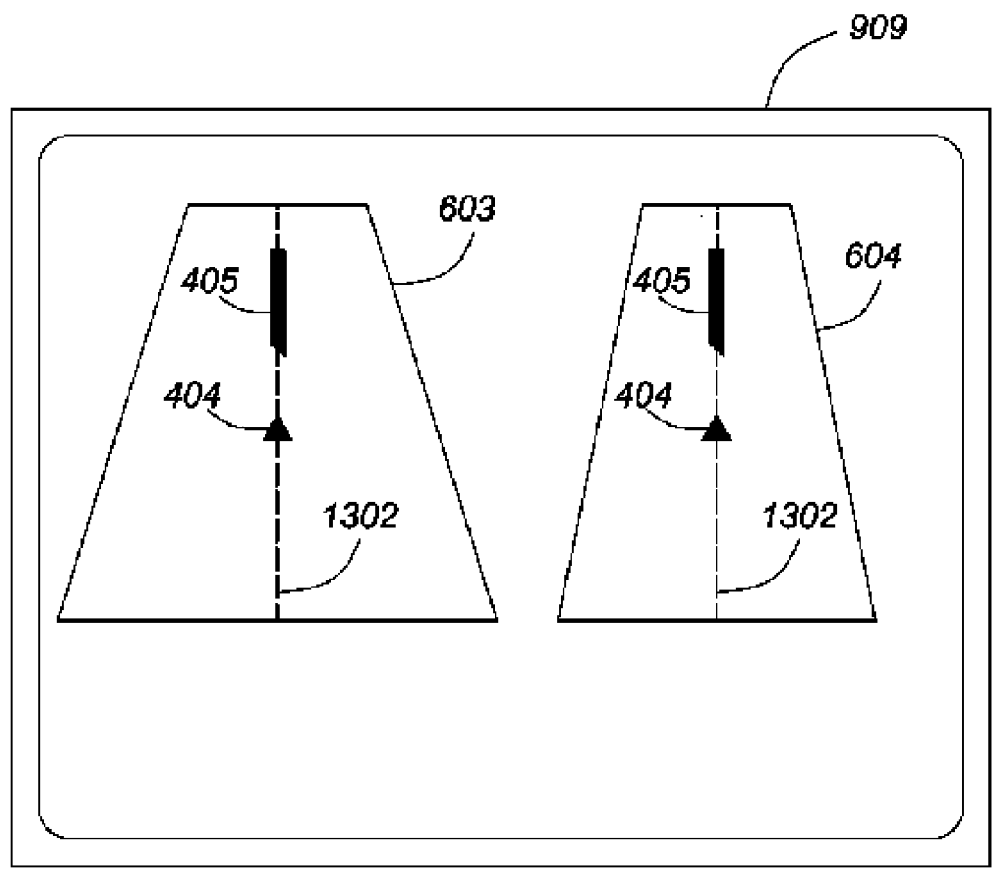
FIG. 11 is a schematic view of a display device displaying multiple images captured by the ultrasound imaging and needle guiding apparatus.

As shown in FIG. 9 and as will be described in more detail below, the apparatus 200 can be coupled to a data processing and display system 900, which includes circuitry 904, 905 for processing volumetric datasets representing the ultrasound images captured by the probe 202, and a display device 909 for viewing the processed ultrasound images. As shown in FIG. 11, the 3-D ultrasound volumetric datasets obtained by the ultrasound probe 202 can be processed and displayed as a single or as multiple image(s) of the volume of interest and the medical instrument 405 inserted into the volume of interest.

Figure 1:
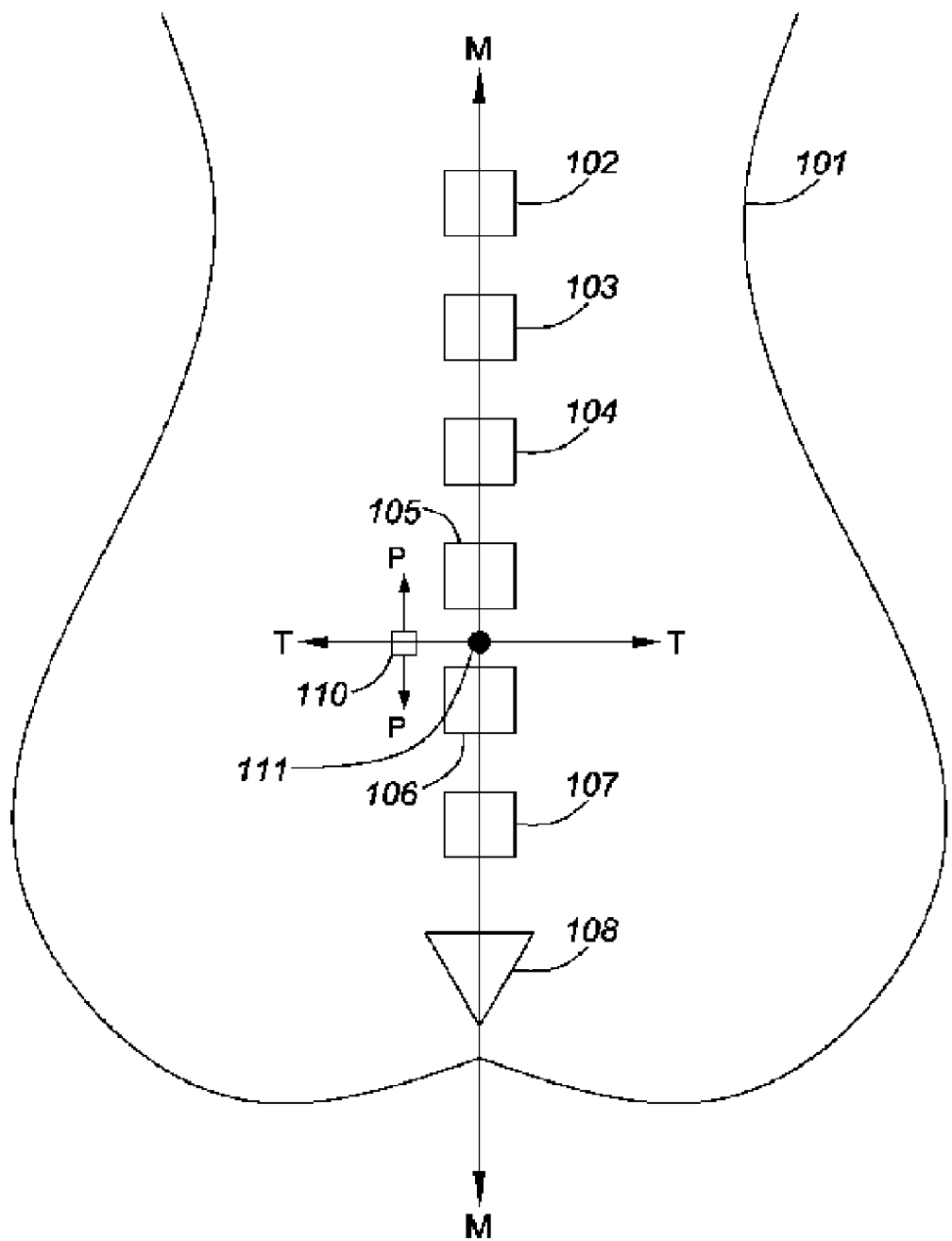
FIG. 1 is a schematic view of approximate locations of vertebrae, needle puncture point, and various imaging planes of a patient to be imaged by an ultrasound probe and subjected to an epidural anesthesia procedure.

One particular application of this apparatus 200 is for imaging the anatomy of a patient's spine and a needle during an epidural injection, in which case the medical instrument 405 is an epidural needle and the target is the epidural space. FIG. 1 shows the lower back of a patient's body 101; the vertebrae of the lower back are the thoracic vertebrae T12 102, lumbar vertebrae L1 103, L2 104, L3 105, L4 106, L5 107 and the sacrum 108. A preferred needle puncture site 111 is located between the third lumbar vertebra L3 105 and the fourth lumbar vertebrae L4 106 in the midline M-M of the patient's spine and along a transverse T-T plane. The apparatus 200 in this application is designed as a portable device that a health care provider can place on the back of the patient undergoing the epidural injection. The apparatus 200 is positioned near the preferred puncture site 111 such that the health care provider may image the back and spine underneath the apparatus 200 and detect in the ultrasound image both the major anatomical features of interest and the tip and body of the needle 405 during the injection. The probe 202 is located on the mount 199 such that when the apparatus 200 is placed on the back of the patient with the medical instrument guide 203 directly above preferred puncture site 111, the probe 202 is located at position 110 directly above the spinae erector muscle; it is expected that the muscle tissue at this location 110 serves as a "window" that transmits ultrasound particularly well. The probe 202 can also be oriented on the mount 199 such that propagation of the sound waves from the probe 202 is directed towards the spine.

The back of the mount 199 (i.e. the portion facing away from the body 101 during use) is provided with a hand grip that is shaped and sized to allow for easy single-handed gripping by the operator. Although not shown, the back of the mount 199 can be further provided with finger grips shaped to accept the fingers of the operator. Alternatively, the apparatus 200 is provided with an easy to grasp handle (not shown) so that the operator may hold the apparatus 200 with one hand comfortably against the patient's back during the procedure. The handle may be a basket type handle or pistol-shaped grip protruding from the back of the mount 199.

The 3-D probe 202 emits sound waves into a 3-D volume that covers the part of the patient's spine underneath the apparatus 200, typically near the L3 and L4 vertebrae. The received data from the reflected sound waves create a volumetric dataset (often abbreviated as "volume") of the anatomy, unlike a 2-D ultrasound probe which creates images of a cross-sectional plane. The 3-D volume can be viewed by the operator in a number of ways, including viewing a 2-D image of a thick slice 403 (see FIGS. 4(a) and 4(b)) of a slab of the volume along a cross-sectional plane of the volume. The 2-D image can be created from the slab of data by merging the data in the direction perpendicular to the cross-sectional plane. The merging involves taking a weighted combination of the data after data conditioning where the weights are chosen to emphasize data representing the instrument and target. The ability to view thick slices 403 of the volume at a location and angle that matches both the needle propagation axis and the target may be a way to alleviate the limitations of conventional 2-D ultrasound transducers. Furthermore, the ability to view thick slices may be a way to alleviate the limitations of standard cross-sectional imaging where needle bending and uncertainty in the location of the needle propagation axis make it difficult to maintain alignment of the needle in the cross-sectional plane, and thus maintain needle and target visibility in the image.

Real-time 3-D ultrasound imaging can be implemented by at least the following two methods:

1) mechanical sweeping: A specialized 3-D probe is constructed by combining a 2-D probe with a motorized mechanism for rapidly moving the 2-D probe so that the 2-D image sweeps repeatedly through a volume of interest. Repeated sweeping is usually implemented in an oscillating manner where each oscillation produces a 3-D volume. The spatial relationship between the set of 2-D images from each oscillation is known because the probe motion is controlled and the images are reconstructed into a 3-D Cartesian volume. This device is referred to hereafter as a mechanical 3-D probe;

2) multidimensional arrays: A specialized probe is created without a motorized mechanism, but instead uses a two dimensional array of transducers to scan over a 3-D volume of interest. The speed of volume acquisition is typically higher than mechanical probes but the complexity of the probe increases and image quality can be inferior. This probe is known as a multidimensional probe.

The 3-D probe 202 of the apparatus 200 can be a mechanical 3-D probe or a multi-dimensional 3-D probe as known in the art. An example of a suitable mechanical 3-D probe is the RAB2-5 H46701M for the Voluson 730 ultrasound machine by General Electric Corporation (GE Healthcare, Chalfont St. Giles, United Kingdom). An example of a suitable multidimensional probe is the X7-2 for the Philips iU22 ultrasound machine (Philips Healthcare, Andover, Mass., USA). With such types of probes, the rapid creation of 3-D volumes allows multiple planes of the acquired volumes to be visualized in real-time, thus overcoming some of the limitations of standard 2-D probes. These planes can be selected at any orientation and location within the volume through user control.

The medical instrument guide 203 in this embodiment is a channel which extends through the mount 199 and is sized to receive the epidural needle 405; although not shown the channel can have a closable cover that extends along part or the entire length of the channel and which can be opened to allow access therein for releasing the needle, cleaning etc. The medical instrument guide 203 is positioned beside the 3-D probe 202 and is used to constrain the path of the epidural needle 405 inserted during the injection procedure. When the apparatus 200 is placed on the patient's back, the axis A-A (see FIG. 2) of the apparatus 200 is aligned approximately to within 10 to 20 degrees, measured about the axis of the medical instrument guide 203, of the midline axis of the spine M-M (see FIG. 1) in the inferior-superior direction, while the axis B-B of the apparatus 200 is orthogonal to axis A-A and is aligned to extend to the left and right of the patient along transverse axis T-T (see FIG. 1). The axis of the medical instrument guide 203 is aligned approximately with the axis C-C which is the horizontal axis extending through the needle insertion point 111 (see FIG. 3) and is directed towards the patient's back in the anterior-posterior direction. The apparatus 200 can be provided with markings (not shown) representing axes A-A, B-B, and C-C to assist the operator in correctly positioning the apparatus 200 against the patient's back during use.

As will be discussed further below, the apparatus 200 obtains volumetric datasets that are processed by the system 900 and displayed in multiple real-time views which assist the operator in guiding the medical instrument 405 to the target. Two of these views include the thick slices along the sagittal plane which is the plane along axes M-M and C-C and the transverse plane which is the plane along axes T-T and C-C.

Figure 14B:
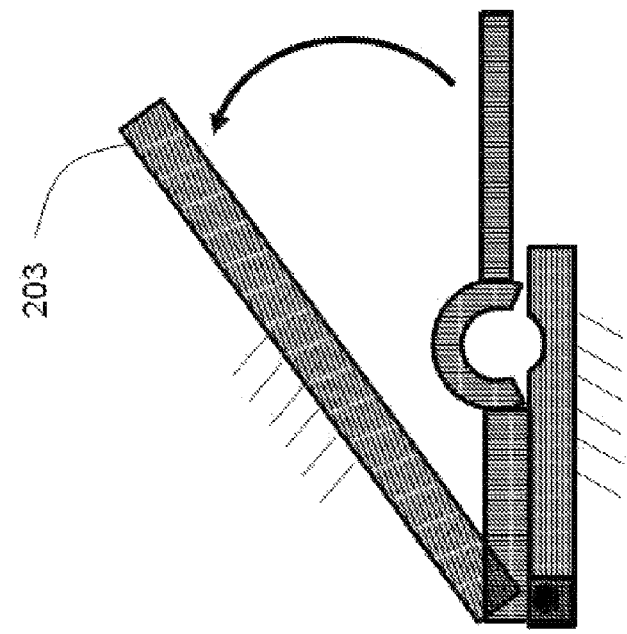
FIG. 14(a) is a schematic front view of a detachable medical instrument guide and FIG. 14(b) is a schematic front view of the detachable medical instrument guide attached to an ultrasound imaging and needle guiding apparatus according to another embodiment.
Figure 14A:
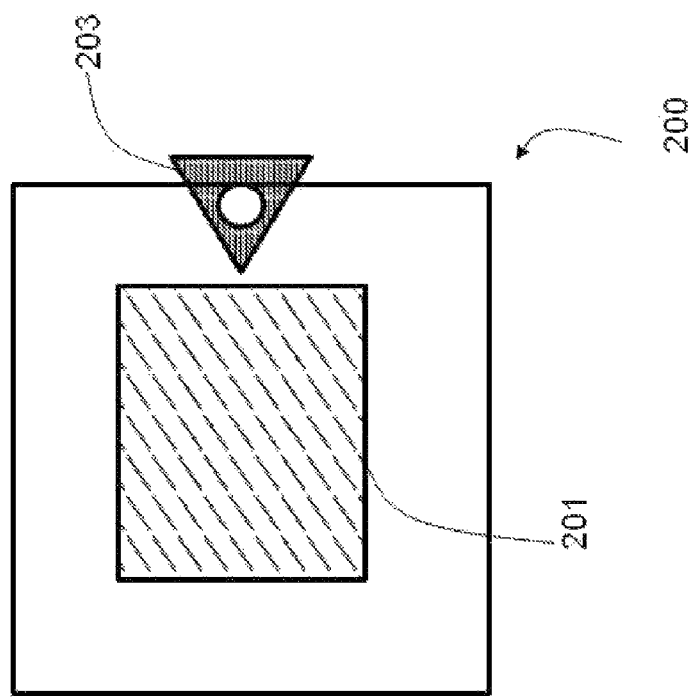

While a channel through the mount 199 serves as the medical instrument guide 203 in this embodiment, the medical instrument guide can be a bore, slot, aperture, hole or any guide-way which serves to constrain the path of the needle 404 during the insertion procedure. Also, the medical instrument guide can either be permanently affixed to the apparatus 200 as shown in FIGS. 2-8 and FIG. 12, or be a separate component which can be detachably mounted to the mount 199 as shown in FIG. 14; in this Figure, the guide 203 is a clip having three members pivotably connected about a pivot axis; the instrument guide 203 can be attached to a channel located beside the probe 202 and at the edge of the mount 199. The detachable medical instrument guide can be designed to allow the selection of a particular trajectory to be chosen by mounting one of a series of medical instrument guides, each with a different orientation of the guide-way. The detachable medical instrument guide and the mount can also be disposable after a single use for the purposes of ease-of-sterilization.

As can be seen in FIG. 4, the probe 202 is positioned and operated so that a portion (shown in cross-hatched shading) of the volume 402 produced by probe 202 intersects the pathway of the needle 405 inserted through the guide 203. FIG. 4(*a*) shows a thick slice 403 portion in the sagittal plane. FIG. 4(*b*) shows a thick slice 403 portion in the transverse plane. The thickness of the slice is typically 5 mm, but other thicknesses can be used, including a thickness of 0 mm, which is considered a simple cross-sectional image with zero thickness. As can be seen in FIG. 5, the instrument guide (bore) 203 and probe 202 locations are positioned relative to each other so that the thick slice portion 403 covers a target 404 which represents the epidural space, and the part of the needle pathway leading up the target 404. In this Figure, the needle 405 is shown partly inserted into the medical instrument guide 203 in a direction that will intersect the target 404.

Referring to FIG. 9, an imaging system 900 incorporating the apparatus 200 processes and displays the images obtained by the apparatus 200. In the system 900 shown in FIG. 9, the probe 202 is connected to a transmit/receive (T/R) switch 901. The T/R switch 901 receives signals from a beam transmitter 902 and outputs signals to the probe 202. The T/R switch 901 also transmits signals from probe 202 to a beam receiver 903 that forms echo signals for processing. Both the beam transmitter 902 and the beam receiver 903 are communicative with and controlled by a system controller 907. The beam receiver 903 outputs echo signals (representing 3-D volume datasets) from probe 202 to a signal processor 904, which performs functions such as, but not limited to, digital filtering, contrast detection and enhancement, spectral analysis and B-mode processing; both beam receiver 903 and signal processor 904 are controlled by the system controller 907. Signal processor 904 outputs the modified echo signals to a 3-D image rendering module 905 which converts the 3-D volume datasets into 2-D images using a method such as, but not limited to, thick reslicing. The 3-D image rendering is performed according to instructions provided by the system controller 907, which can receive input from a user interface 908 to determine methodology. 2-D image data sets are transferred into an image memory 906 for access by the user interface 908, for display on a 2-D image display 909 such as a computer screen, and/or for long term storage on a storage device 910 such as a hard drive. The image memory 906 communicates with the system controller 907 and the user interface 908 to access datasets and control filing. The user interface 908 can receive commands from a user to control the operation of the system 900, how image data is processed and displayed on the 2-D image display 909, and to access/store images in the long-term image storage device 910. The user interface 908 includes an interface program that may be integrated with the 2-D image display 909 and may include, but is not limited to, a pointing device such as a mouse or touch screen, a keyboard, or other input devices such as a microphone. The system controller 907 communicates with user interface 908 to relay operational and display instructions and operational status. The system controller 907 communicates with the 2-D image display 909 to synchronize the data stream.

Figure 10:
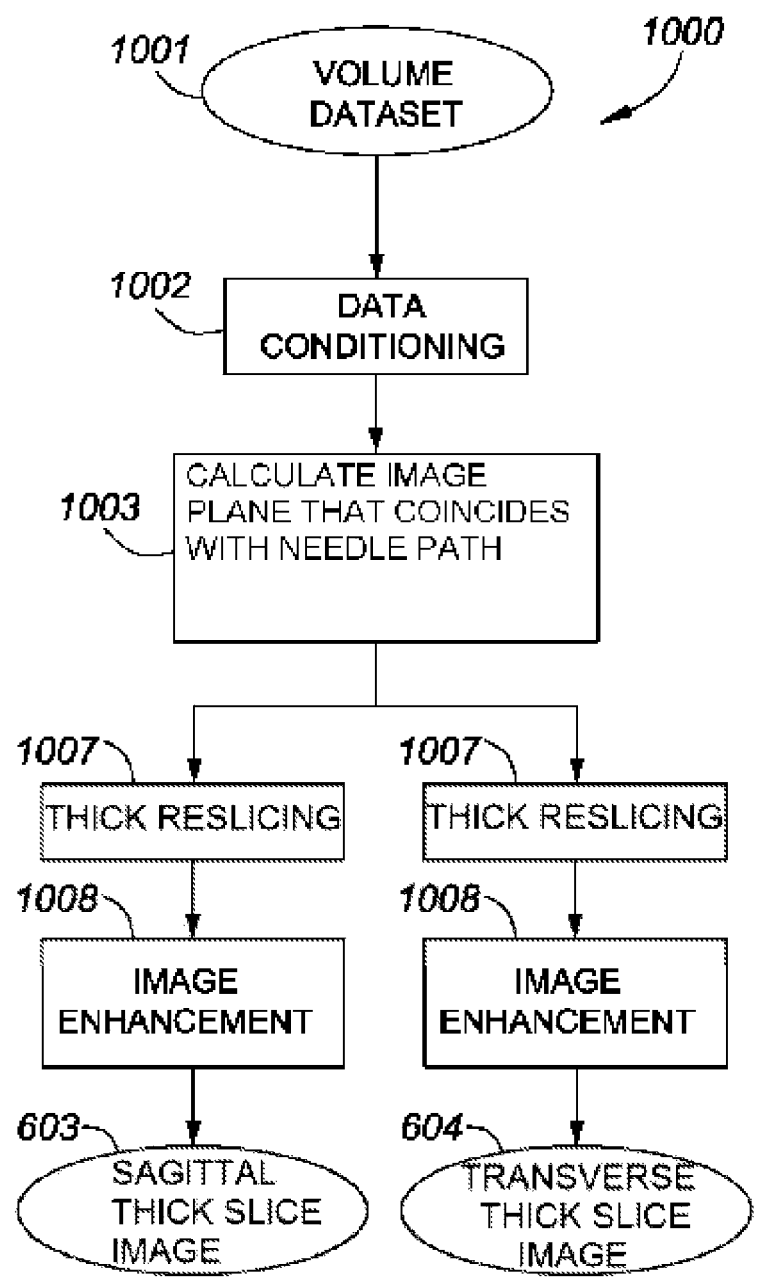
FIG. 10 is a flow chart of a method for processing data from the 3-D volumetric datasets captured by the ultrasound imaging and needle guiding apparatus.

Referring to FIG. 10, a data processing method 1000 is carried out by the system 900 to manipulate the 3-D volumetric dataset 402 acquired by the apparatus 200 to produce a 2-D thick slice sagittal plane image 603 and a 2-D thick slice transverse plane image 604, which can be displayed on the display device 909. First, the volumetric dataset 402 is obtained from the apparatus 200 (step 1001) and transmitted via T/R switch 901 and beam receiver 903 to the signal processor 904 for data conditioning (step 1002). Data conditioning performed on the 3-D volumetric dataset 402 may include, but is not limited to: filtering, enhancement, thresholding, smoothing and feature extraction. The signal processor 904 also calculates the thick slice portion of the volume 403 (step 1003). The thick slice portion 403 is then transmitted to the image rendering device 905 for thick slice cross-sectional (step 1007) image processing.

Instead of a separate signal processor 904, image rendering module 905, controller 907 and memory 906, the steps of the method shown in FIG. 10 can be stored on computer readable medium that can be executed by a general purpose computing device. Examples of suitable computer readable medium are compact disk read only memory (CD-ROM), random access memory (RAM), or a hard drive disk.

When carrying out the thick slice image processing in step 1007, the slab of data used to create the 2-D thick slice image can be taken from the thick slice portion 403 encompassing the sagittal plane, and transverse plane (which are the planes that intersect the medical instrument guide for needle insertion), or on another image plane inputted by the user or automatically selected. Conversion of the slab of data in the thick slice portion 403 into a 2-D thick slice image can be performed by merging the data in the direction perpendicular to the cross-sectional plane of the slab. The merging of the data in the perpendicular direction is performed by weighted averaging after data conditioning. The weighting of the data points is chosen to enhance the depiction of the instrument and target.

The resultant 2-D thick slice image is then processed by the rendering device 905 for image enhancement 1008 which may include, but is not limited to, filtering, enhancement, thresholding, smoothing, feature extraction and graphical overlays 1302 (see FIG. 11) and results in the final images. In particular, a graphical overlay of the anticipated needle trajectory can be superimposed onto the thick slice images. The location of the overlaid trajectory is known and fixed relative to the probe 202, because it is determined by the physical location of the medical instrument guide 203 on the apparatus 200. The enhanced images are then ready for display by display device 909, and/or storage on storage device 910. The final images are the thick slice sagittal image 603 and the thick slice transverse image 604.

The thick slice transverse image 604 coincides with a plane that is transverse to the patient and intersects the trajectory 1302 of the medical instrument guide 203. This transverse plane, in which thick slice image 604 is formed, can be the same plane as shown FIG. 3. As the operator inserts the needle 405 into the tissue, the needle 405 becomes visible in the image 604, and will be along a graphic overlay 1302 of the expected needle trajectory. As the needle 405 is inserted deeper into the tissue, more and more of the needle becomes visible in the image 604. The operator aligns the needle trajectory 1302 with the target 404 so that subsequent insertion of the needle 405 into tissue reaches the target 404. This image 604 is updated on the display device 909 as the ultrasound 3-D volumetric dataset 402 is created by probe 202. In this way, the apparatus 200 provides current images of the needle insertion procedure.

Similar steps as described above can be applied to produce the thick slice sagittal image 603.

Conventional 2D cross-sectional ultrasound imaging has several limitations that prohibit ultrasound guidance of a needle to the epidural space in the spine. The first limitation is the inability to depict clearly the target epidural space when the probe is placed in the mid-sagittal plane (also known as the median longitudinal plane) where the needle insertion usually takes place. The reason that the epidural space does not appear clearly in this view is because of the presence of the interspinous ligament and spinous processes that fall in the mid-sagittal plane and these structures do not allow the ultrasound beam to penetrate to the epidural space located beneath these structures. It is well known that the target epidural space is best imaged by ultrasound in the paramedian plane, where the ultrasound probe is placed on the spinae erector muscle on the left or right of the mid-sagittal plane. A second limitation of conventional 2D ultrasound is that a paramedian placement of the probe means that the imaging plane does not coincide with the plane of needle insertion, so it is impossible to see both the needle in the imaging plane during the entire time it is being inserted. A third limitation is that placing the conventional 2D ultrasound probe in the mid-sagittal plane obscures the puncture site of the needle. What is needed is a solution that combines paramedian placement of the probe with high-quality depictions of both the epidural space and needle in the same image.

The above described embodiments provide this solution by using thick-slice imaging from a 3D ultrasound probe. The probe can be placed paramedian to the mid-sagittal plane and a volumetric dataset is acquired over a volume that includes the mid-sagittal plane. The thick slice image in the sagittal plane is created from a slab of data that extends a few millimeters to the sides of the mid-sagittal plane. A slab thickness of a few millimeters is sufficient to include a clear depiction of the target epidural space. During ultrasound scanning, the needle is inserted in the mid-sagittal plane and the highly reflective nature of the needle means it appears clearly in the slab of ultrasound data. By combining together the data in the slab into the thick slice image, both the needle and target can be clearly seen.

Operation

Figure 13:
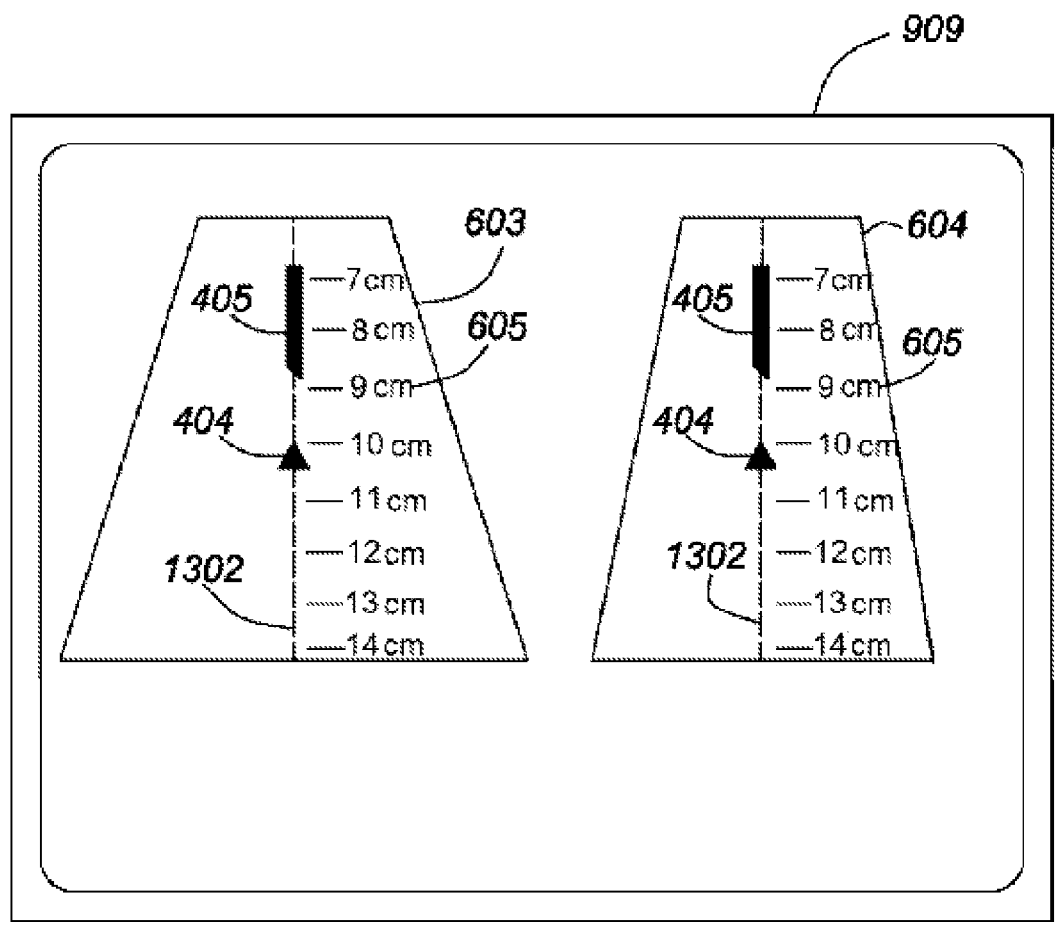
FIG. 13 is a schematic view of a display device displaying multiple images captured by the ultrasound imaging and needle guiding apparatus, according to another embodiment of the invention, along with centimeter graduations on the overlay of the calculated anticipated trajectory of the needle.

For example to illustrate operation of the embodiments of the invention, in performing an epidural anesthesia procedure on a patient using the apparatus 200, an operator holds the apparatus 200 with one hand gripping the handle and places the apparatus 200 against the patient's back so that the medical instrument guide 203 is directly over the needle insertion point 111. The operator then activates the apparatus 200 to cause ultrasound signals to be emitted by the probe 202 and consequent data to be collected and processed by the system 900 and displayed as 2-D images on the display device 909. The operator aligns the displayed target 404 (e.g. the epidural space) with the superimposed anticipated needle trajectory 1302 in the ultrasound image(s). The operator can then insert the epidural needle 405 through the medical instrument guide 203 with the hand that is not gripping the apparatus 200. The operator may then view in real time on the display device 909 a processed ultrasound image of the needle tip and needle body and the patient's back and spine, such as the two thick slice images of the sagittal and transverse planes as shown in FIG. 13. The operator may then determine, by viewing the relative motion of the needle tip with respect to the spinal anatomy, when the needle 405 has reached the epidural space of the spine. Optionally, the operator then detaches the needle 405 from the medical instrument guide 203 so that the operator can use both hands to perform a loss-of-resistance to saline procedure to ensure the needle 405 has reached the target 404 (epidural space) and insert a catheter or inject an anesthetic agent.

As can be appreciated from the above discussion, one advantage of this apparatus 200 is the ability to capture an image of the target, nearby anatomy, and needle trajectory for display in the same display device. Another advantage is the ability to acquire more than one image of the target, nearby anatomy and needle trajectory through the use of a 3-D ultrasound probe. Yet another advantage is the ability to use the optimal locations on the skin surface, also known as "windows", for viewing the spine with ultrasound. Yet another advantage is the ability to place the needle through the medical instrument guide 203 near the middle of the apparatus 200 so that the footprint of the apparatus 200 does not interfere with the puncture site of the needle 405. Yet another advantage is the use of thick slice images that depict the needle and target clearly even when the needle path has small deviations from the transverse and sagittal cross-sections of the volume.

Other Alternate Embodiments

According to another embodiment, the operator performs the loss-of-resistance technique or catheter insertion or administration of anesthetic or analgesic while the needle 405 is still inserted into the medical instrument guide 203. This embodiment has the advantage of reducing the number of steps before catheter insertion or injection of anesthetic agent.

Figure 2:
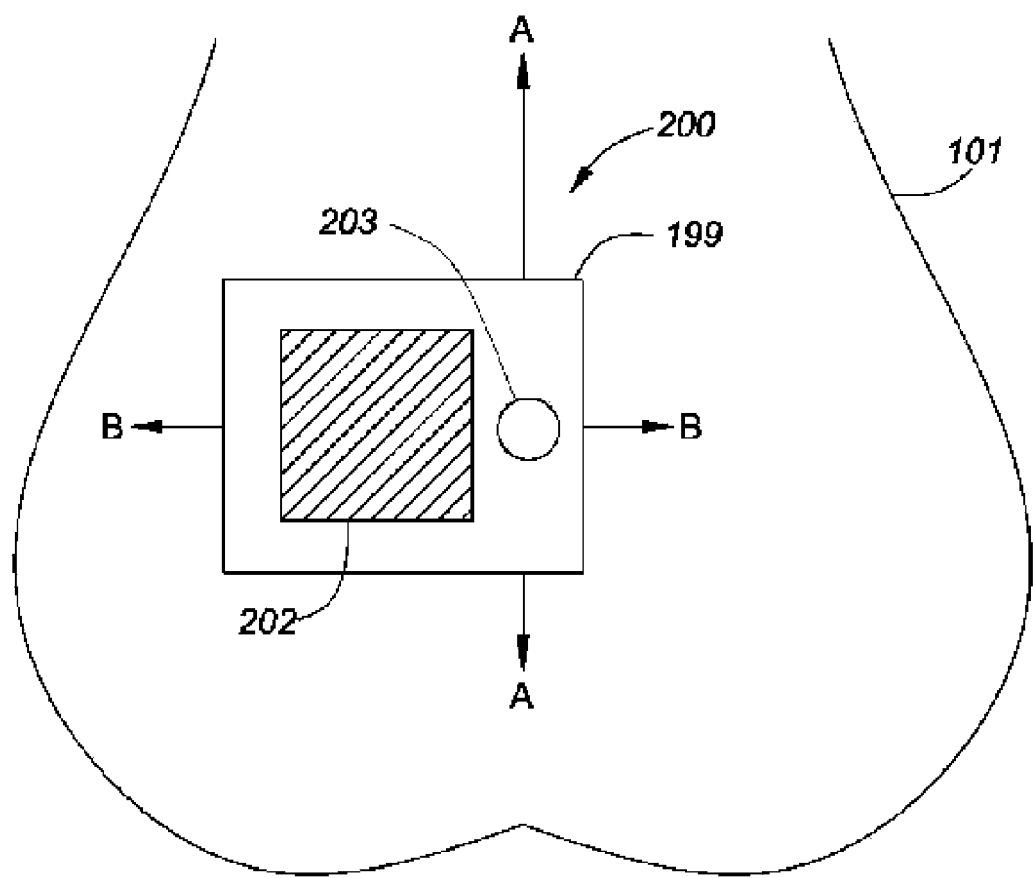
FIG. 2 is a schematic back view of a 3-D ultrasound imaging and needle guiding apparatus according to one embodiment of the invention and positioned to image the spine of the patient shown in FIG. 1.
Figure 3:
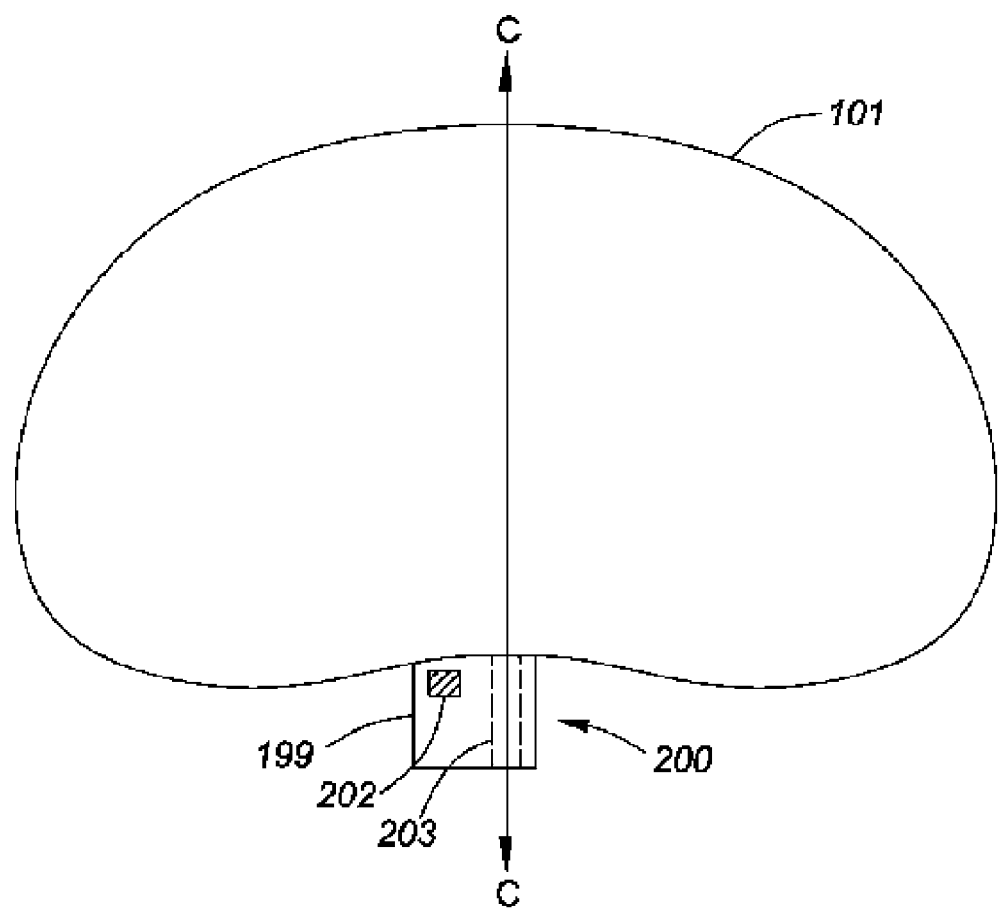
FIG. 3 is a schematic top view of the ultrasound imaging and needle guiding apparatus and a cross-section of the patient's torso.
Figure 15:
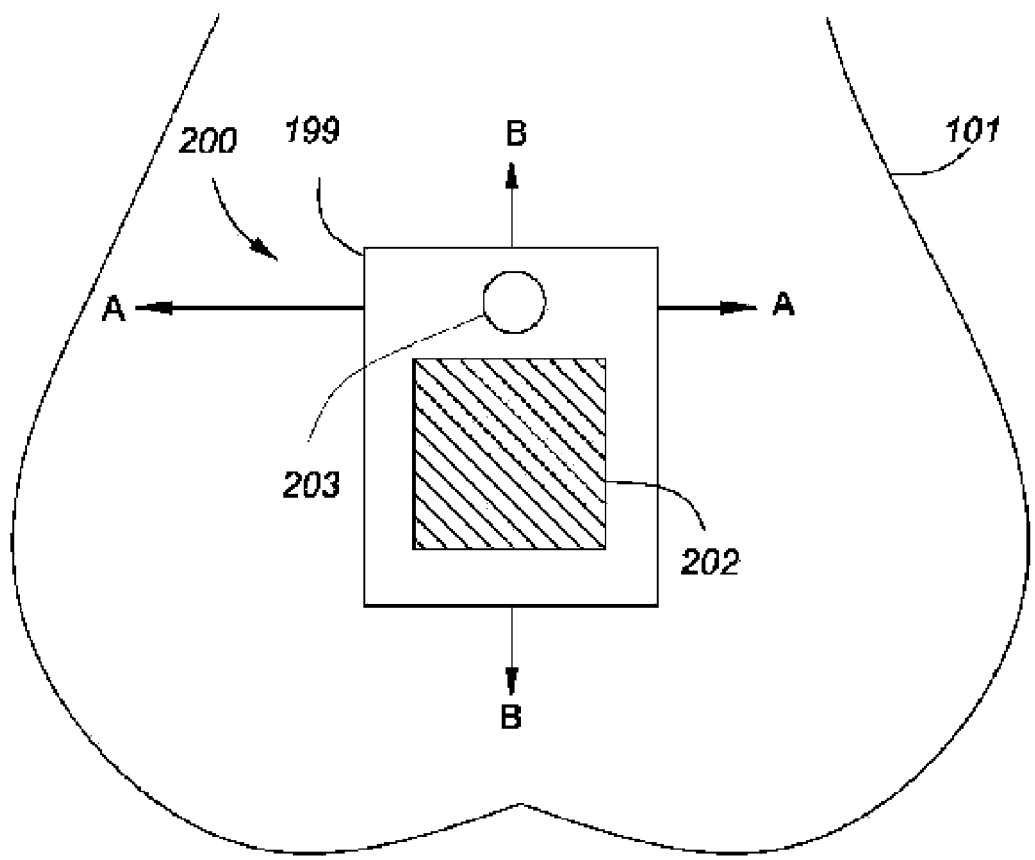
FIG. 15 is a schematic back view of a 3-D ultrasound imaging and needle guiding apparatus according to another embodiment of the invention and positioned to image the spine of the patient from a midline axis of the spine, and rotated ninety degrees from the position indicated in FIG. 2.

Referring to FIG. 15 and according to another embodiment, the apparatus 200 can be used in an orientation different than that shown in FIG. 2. In the orientation shown in FIG. 15, the axis B-B of the apparatus 200 is aligned approximately to the midline of the spine M-M (see FIG. 1), while the axis A-A is aligned approximately to the left and right of the patient along transverse axis T-T (see FIG. 1). In this orientation, the axis of the medical instrument guide 203 is aligned with the axis C-C, which is the horizontal axis extending through the needle insertion point 111 (see FIG. 3) and is directed towards the patient's back in the anterior-posterior direction. A thick slice 403 of the volume in the plane containing the axes A-A and C-C covers anatomy from both the left and right side of the spine, so the symmetry of the spine's appearance in the image can be used for adjusting the position of the apparatus 200 such that the axis C-C of the medical instrument guide intersects the midline axis of the spine M-M. This embodiment has the advantage that the operator may mark the skin surface at the centerline of the spine to create a visual aid for faster positioning of the apparatus as shown in FIG. 2 for subsequent needle insertion.

Referring to FIG. 2 and according to another embodiment, the apparatus 200 can be used in an orientation flipped to the right side of the body (not shown). This embodiment is simply the mirror version of the placement of apparatus shown in FIG. 2, where the probe is instead placed on the right side of the body. This embodiment has the advantage of allowing an operator to use the right hand to hold the apparatus 200, and the left hand to insert the needle for operators who are left-handed. In FIG. 2, the apparatus 200 is held in the left hand and the right hand is used to insert the needle.

Figure 6:
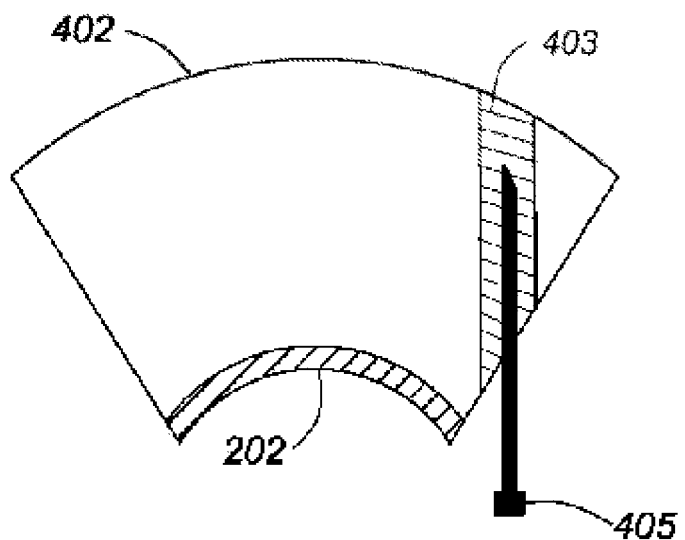
FIG. 6 a schematic top view of a curved ultrasound probe of the imaging and needle guiding apparatus according to another embodiment of the invention, along with a representation of the spatial extent of the volumetric dataset captured by the ultrasound probe.

Referring to FIG. 6 and according to another embodiment, the probe 202 is curved. In this embodiment, the size and shape of the 3-D volume 402 are determined by the curved shape of the probe 202. This embodiment has the advantage of obtaining a wide field of view of the anatomy with a relatively small footprint of the probe due to the curvature of the face of the probe that produces a diverging set of beams that are used to form a 2-D image or 3-D volumetric dataset. This embodiment also has the advantage of directing the ultrasound beams toward the needle 405 at an angle that is closer to perpendicular to the needle 405, resulting in a stronger echo from the needle 405 and a better depiction of the needle 405 in the 3-D volumetric dataset.

In yet another embodiment (not shown), the probe 202, whether flat or curved, can be further angled toward the medical instrument guide 203 so that the beams intersect the needle at angles even closer to perpendicular.

Figure 7:
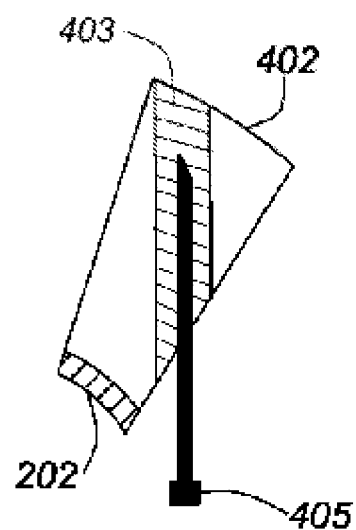
FIG. 7 a schematic top view of a curved ultrasound probe of the imaging and needle guiding apparatus according to another embodiment of the invention, along with a representation of the smallest spatial extent of the volumetric dataset captured by the ultrasound probe that encloses the thick slice.

Referring to FIG. 7 and according to another embodiment, the probe 202 images the smallest volume 402 that encloses the thick slice 403. This embodiment has the advantage of acquiring a smaller volume at a faster rate than a larger volume, which allows faster processing by the imaging system 900.

Figure 8:
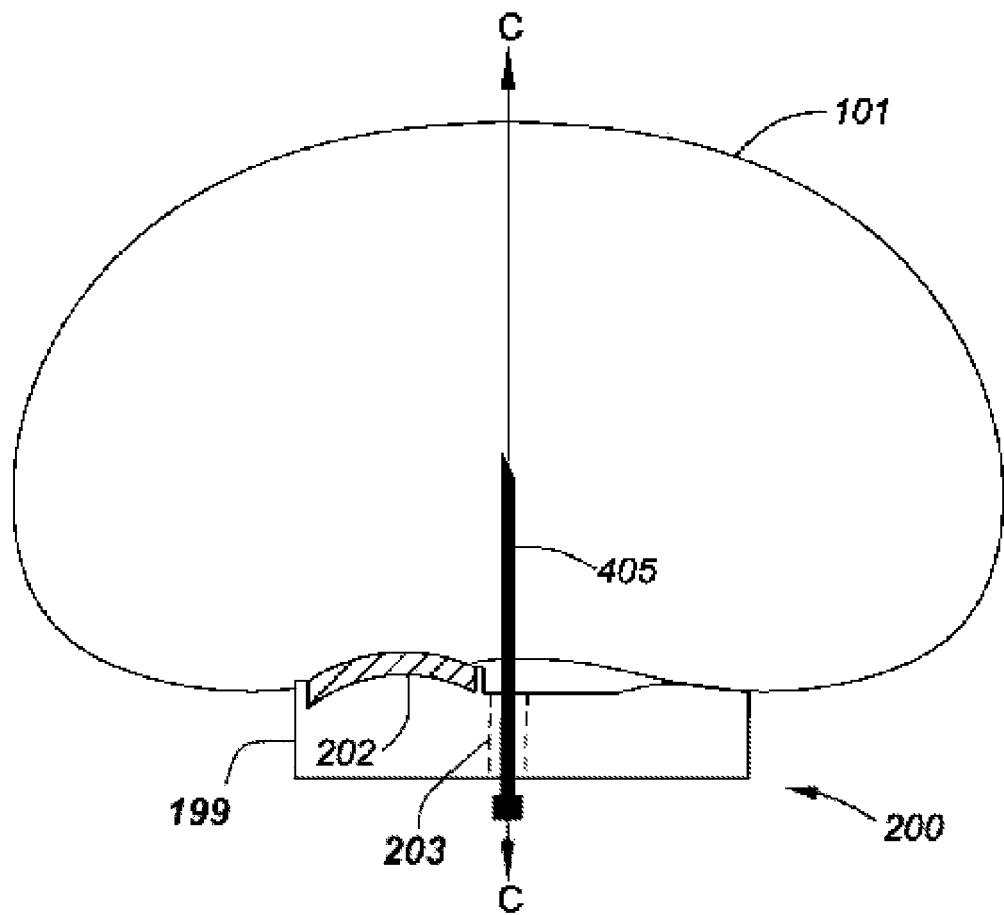
FIG. 8 is a schematic top view of the ultrasound imaging and needle guiding apparatus, according to another embodiment of the invention, along with a mount having a second contact that stabilizes the apparatus on the patient, and a cross-section of the patient's torso.

Referring to FIG. 8 and according to another embodiment, the mount 199 is shaped so that it comes in contact with the body 101. This embodiment has the advantage that the mount 199 creates a second contact point with the body 101, in addition to the contact point from the probe 202, and the second contact point provides additional stability for the apparatus 200 with respect to the patient.

Figure 12:
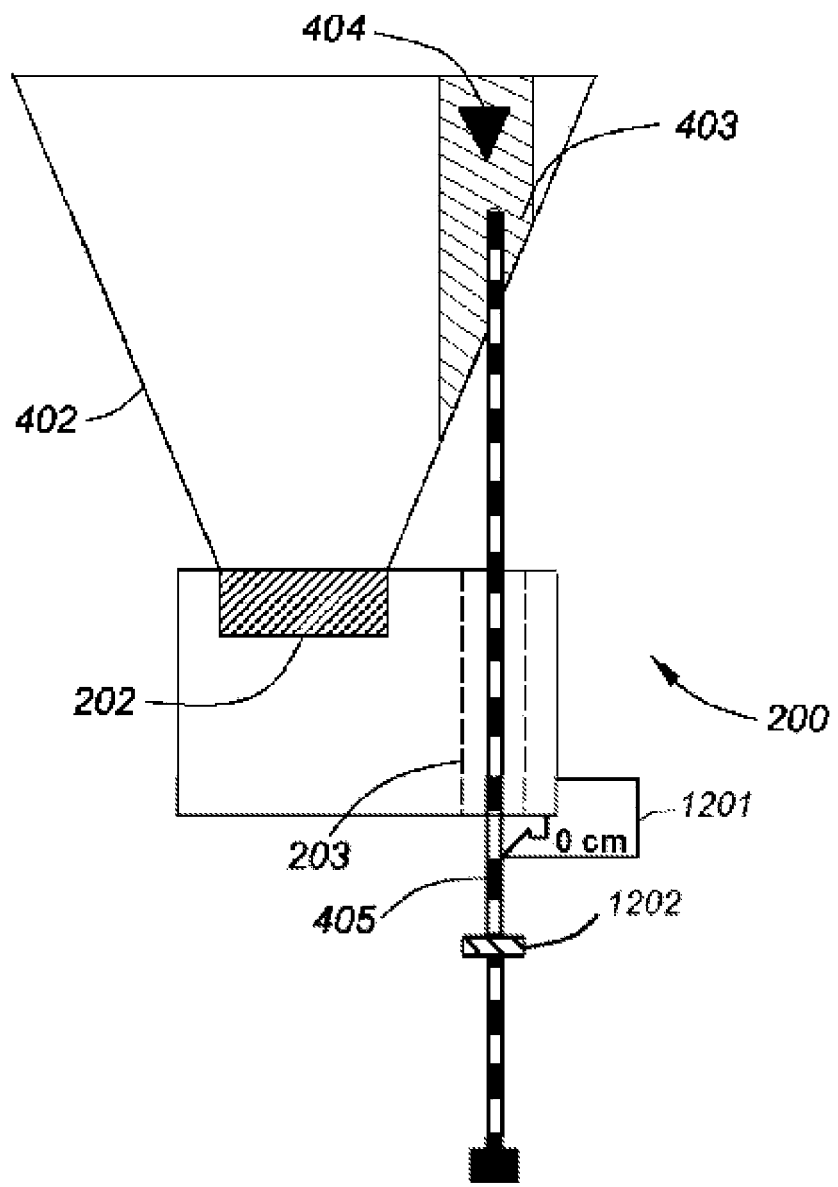
FIG. 12 is a schematic top view of the ultrasound probe of the ultrasound imaging and needle guiding apparatus, according to another embodiment of the invention, along with a representation of the spatial extent of the volumetric dataset captured by the ultrasound probe, and an indicator mark for the origin of the depth measurements of the needle insertion.

Referring to FIG. 12 and according to another embodiment, the medical instrument guide contains a mark 1201 or other indication for the origin of the measurement of the needle insertion depth. This embodiment has the advantage of using the fact that most epidural needles have a series of black etchings spaced 1 cm apart (see FIG. 12) to allow the operator to count the centimeters of needle insertion relative to graduations shown on the 2-D ultrasound image. The graduations 605 are shown in FIG. 13 as graphical overlays superimposed on the thick reslice images 603 and 604. With this embodiment the operator aligns the displayed target 404 (e.g. the epidural space) with the superimposed anticipated needle trajectory 1302 in the ultrasound image(s) and observes the depth of the target 404 relative to the graduations 605. In FIG. 12, the target is at 10 cm depth, as an example. The needle 405 is subsequently inserted through the medical instrument guide 203 while the depth of insertion is observed by counting the centimeter etchings on the needle relative to the mark 1201. The operator stops insertion of the needle 405 at a depth less than or equal to the depth of the target 403, as determined by counting. This embodiment has the advantage that the needle 405 does not need to be clearly visible in the display device 909, only the target 403 needs to be visible, and that overshoot of the needle 405 past the target 403 can be avoided by observing the depth of the insertion of the needle 405.

According to yet another embodiment, a component of the medical instrument guide, such as a rubber grommet 1202 (see FIG. 12), is attached by the operator to the needle 405 at the depth of the target 403 as indicated by the graduations 605 that are related to the origin at the mark 1201. The grommet is attached before needle insertion and serves as a visual aid to ensure that the needle 405 insertion does not overshoot the target 404. As an example, in FIG. 12 and FIG. 13, the target depth is 10 cm and the needle is shown inserted to a depth of 9 cm, so the grommet is 1 cm away from the mark. This embodiment has the advantage that the operator does not need to count the black etchings relative to the mark 1201, but only needs to stop insertion of the needle 405 when the grommet reaches the mark 1201.

According to yet another embodiment (not shown), the needle guide 203 is not permanently or detachably mounted to the mount 199 and instead is a component of the apparatus 200 that is located remotely of the probe 202 and mount 199. Both the apparatus 200 and needle 405 are provided with a position tracking system that provides measurements of the needle location and orientation relative to the ultrasound probes. The tracking system can be based on electromagnetic tracking of coils placed on both the needle 405 and the apparatus 200. A tracking system can also be based on optical tracking of visible fiducials placed on both the needle 405 and the apparatus 200. Furthermore, a tracking system can be based on a moveable needle guide connected to the apparatus 200 by one or more linkages with angle sensors on the linkage joints. With any such needle position tracking system, the expected needle trajectory can be calculated from the measured needle location and orientation. This expected needle trajectory can be shown as a graphic overlay 1302 on any of the images 603 or 604. In use, the operator can position the needle guide 200 such that the propagation axis of the projected trajectory will fall within the volume 402 of the probe 202 and thus be displayable on the display device 909.

According to yet another embodiment (not shown), the needle guide 203 is permanently or detachably mounted to the mount 199, and is used together with a position tracking system to provide measurements of both the apparatus 200 and needle 405 relative to the probe 202. The needle guide 203 determines the fixed propagation axis of the needle 405 and the position tracking system determines the location of the needle along the propagation axis. This embodiment has the advantage of constraining the needle to a fixed propagation axis with respect to the apparatus, which improves ease-of-use, combined with measurements of the location of the depth of needle insertion from the position tracker. By using both a needle guide 203 and position tracking, the location of the needle tip can be shown graphically on the monitor 909 using the position tracker measurements, while retaining the fixed trajectory 1302 and graduations 605. This also has the advantage of not requiring clear visibility of the needle 405 in the images 603 and 604.

According to yet another embodiment, the apparatus 200 is first positioned left of the sacrum 108 (see FIG. 1) so that the display of the sagittal thick slice image 603 shows the sacrum 108. The apparatus 200 is then moved up by the operator along axis P-P so that it slides along the side of the spine until it reaches the position 110. The advantage of this operation of the device is that the operator can count the vertebrae as the apparatus slides from the sacrum 108, then past L5 107 and L4 106 until it reaches the position 110. By counting the number of vertebrae displayed on the monitor 909 as the apparatus 200 moves past the vertebrae, the operator can select the desired intervertebral space for the needle insertion, which is normally between L3 105 and L4 106 for epidurals, as shown in FIG. 1. A different desired intervertebral space can be chosen by counting a different number of vertebrae from the sacrum 108 as the apparatus 200 is moved along axis P-P.

In yet another embodiment, the apparatus is first positioned left of T12 102 and moved along axis P-P down the spine until it reached position 110. The vertebra T12 102 is the lowest vertebra that contains a rib, so it can be recognized uniquely in the thick slice images 603 and 604. Similar to counting vertebrae up from the sacrum until the apparatus 200 reaches the desired vertebral interspace, this embodiment counts down from T12. A different desired intervertebral space can be chosen by counting a different number of vertebrae from T12 102 as the apparatus 200 is moved along axis P-P.

While specific embodiments have been described and illustrated, such embodiments should be considered illustrative only and not as limiting the invention.

What is claimed is:

1. A system for acquiring and displaying ultrasound medical images, comprising:
   an ultrasound imaging and instrument guiding apparatus which comprises:
   a hand-held ultrasound probe, configured to acquire a volumetric dataset representing a 3-D depiction of a volume;
   a mount to which the probe is mounted; and
   a medical instrument guide positionable relative to the ultrasound probe and configured to receive and guide a medical instrument along a propagation axis to a target in a body such that the target and the propagation axis intersect in the volume;
   circuitry communicative with the ultrasound imaging and instrument guiding apparatus to receive the volumetric dataset therefrom and comprising a processor with a memory having programmed thereon steps and instructions for execution by the processor to:
   condition the volumetric datasets;
   calculate an image plane that coincides with the propagation axis;
   create a thick-slice image, wherein the thick-slice image represents data from a slab of non zero thickness of the volume encompassing the calculated image plane; and
   a display device communicative with the circuitry to receive and display one or more of the thick-slice images.

2. The system as claimed in claim 1, wherein the memory is further programmed to enhance the thick-slice image.

3. The system as claimed in claim 1, wherein the memory is further programmed to superimpose a graphical overlay representing the propagation axis of the instrument on the image.

4. The system as claimed in claim 1, wherein the medical instrument guide has a visible mark from which the depth of the medical instrument insertion along the propagation axis can be referenced and the memory is further programmed to superimpose a graphical overlay representing and anticipated trajectory of the medical instrument including graduations indicating the depth of the medical instrument inserted with respect to visible mark on the medical instrument guide.

5. The system as claimed in claim 1 further comprising a storage device to record the thick-slice image.

6. The system as claimed in claim 1, wherein the thick slice of the volume is oriented in the sagittal plane of the body.

7. The system as claimed in claim 1, wherein the thick slice of the volume is oriented in the transverse plane of the body.

8. The system as claimed in claim 1, wherein the image is created from the thick slice of the volume by a process of merging data in a direction perpendicular to the cross-sectional plane of the thick slice.

9. The system as claimed in claim 1, wherein the size of the volume acquired by the probe is determined so that it minimally encompasses the maximum extents of the thick slice used to create the image.

10. The system as claimed in claim 4, wherein the visible mark of the medical instrument guide is referenced to show the depth of the thick slice of the volume along the propagation axis.

11. The system as claimed in claim 1, wherein the probe is a mechanical 3-D probe or a multidimensional probe.

12. The system as claimed in claim 1, wherein the probe is curved.

13. The system as claimed in claim 1, wherein the probe is angled towards the propagation axis.

14. The system as claimed in claim 1, wherein the mount is a housing that houses the probe and the medical instrument guide is a channel extending through the housing.

15. The system as claimed in claim 1, wherein the medical instrument guide is detachably mountable to the mount in one or more orientations.

16. The system as claimed in claim 1, the apparatus further comprising a grommet to be attached to the medical instrument at a location relative to the visible mark thereby indicating a desired depth of the medical instrument insertion.

17. The system as claimed in claim 1, wherein the medical instrument guide comprises means for tracking the position of the instrument relative to the probe.

18. The system as claimed in claim 1, wherein the ultrasound probe is configured to acquire the volumetric dataset continuously so that the volumetric dataset comprises real-time or semi-real-time information about the medical instrument's position relative to the target in three dimensions.

19. The system as claimed in claim 1, wherein the ultrasound probe is configured to acquire the volumetric dataset for the smallest volume that encloses the medical instrument and the target.

20. The system as claimed in claim 1, wherein the mount comprises a second contact that is to be in contact with the body in addition to the probe.

21. The system as claimed in claim 1, wherein the mount comprises markings representing the inferior-superior and left-right axes of the body thereby indicating the desired position of the apparatus on the body.

22. A method of using an ultrasound imaging and medical instrument guiding apparatus in an epidural anesthetic procedure, the apparatus comprising:
   a hand-held ultrasound probe, configured to acquire a volumetric dataset representing a 3-D depiction of a volume;
   a mount to which the probe is mounted; and
   a medical instrument guide positionable relative to the ultrasound probe and configured to receive and guide a medical instrument along a propagation axis to a target in a body such that the target and the propagation axis intersect in the volume;
   wherein the volumetric dataset comprises information about the medical instrument's position relative to the target in three dimensions and the medical instrument guide has a visible mark from which the depth of the medical instrument insertion along the propagation axis can be referenced;
   the method comprising:
   placing the apparatus over a back of a patient such that the medical instrument guide is placed over a needle insertion point on the back, and
   emitting an ultrasound signal into the back and acquiring a volumetric dataset representing a 3-D depiction of a volume, wherein the volumetric dataset includes a section of the patient's spine.

23. The method as claimed in claim 22, wherein the target is an epidural space.

24. The method as claimed in claim 22, wherein the probe is placed at a paramedian location with respect to the spine.

25. The method as claimed in claim 22, wherein the probe is placed over spinae erector muscles of the patient.

26. The method as claimed in claim 24, wherein the image plane is approximately in the mid-sagittal plane of the spine or is approximately perpendicular to the long axis of the spine.

27. The method as claimed in claim 22 further comprising inserting a needle through the medical instrument guide and along the propagation axis that intersects the target, such that the captured images includes an image of the needle.

28. The method as claimed in claim 22 further comprising performing a loss-of-resistance procedure to confirm entry of the needle tip into the epidural space.

29. The method as claimed in claim 22 further comprising removing the needle from the medical instrument guide and performing a loss-of-resistance procedure to confirm entry of the needle tip into the epidural space.

30. The method as claimed in claim 22 further comprising placing the apparatus paramedian to the sacrum and sliding the apparatus in the cranial-caudal direction while counting the vertebrae displayed on the image and stopping at the location where the medical instrument guide is placed over the needle insertion point on the back.

31. The method as claimed in claim 22 further comprising placing the apparatus paramedian to the twelfth vertebrae and sliding the apparatus in the cranial-caudal direction while counting the vertebrae displayed on the image and stopping at the location where the medical instrument guide is placed over the needle insertion point on the back.

32. The method as claimed in claim 22, wherein the probe is placed along the midline centre of the spine and the image of the volume is created from a thick slice of the volume approximately perpendicular to the long axis of the spine.

33. The method as claimed in claim 22, wherein the medical instrument guide has a visible mark from which the depth of the medical instrument insertion along the propagation axis can be referenced and the memory is further programmed to superimpose a graphical overlay representing an anticipated trajectory of the medical instrument including graduations indicating the depth of the medical instrument insertion with respect to the visible mark on the medical instrument guide; the method further comprising:
   observing the depth of the target according to the graduations on the graphic overlay with respect to the visible mark on the medical instrument guide;
   inserting the medical instrument through the medical instrument guide, wherein the medical instrument has a plurality of equally spaced etchings; and
   stopping the medical instrument insertion when the depth of the medical instrument insertion, as indicated by the number of the etchings that passed the visible mark, equals the depth of the target.

34. The method as claimed in claim 22, wherein the medical instrument guide has a visible mark from which the depth of the medical instrument insertion along the propagation axis can be referenced and the memory is further programmed to superimpose a graphical overlay representing an anticipated trajectory of the medical instrument including graduations indicating the depth of the medical instrument insertion with respect to the visible mark on the medical instrument guide; the method further comprising:
   observing the depth of the target according to the graduations on the graphic overlay with respect to the visible mark on the medical instrument guide;
   attaching the grommet to the medical instrument at a distance from the inserted tip of the instrument that is equal to the depth of the target with respect to the visible mark on the medical instrument guide;
   inserting the medical instrument through the medical instrument guide; and
   stopping the medical instrument insertion when the depth of the medical instrument insertion, as indicated by the distance from the grommet to the visible mark on the medical instrument guide, equals the depth of the target.

* * * * *